US011259891B2

(12) United States Patent
Girgenti et al.

(10) Patent No.: US 11,259,891 B2
(45) Date of Patent: *Mar. 1, 2022

(54) BREAST BIOPSY LATERAL ARM SYSTEM

(71) Applicant: Hologic, Inc., Marlborough, MA (US)

(72) Inventors: John Girgenti, New Milford, CT (US); Kenneth F. DeFreitas, Patterson, NY (US); Thomas W. DeYoung, Hopewell Junction, NY (US)

(73) Assignee: Hologic, Inc., Marlborough, MA (US)

(*) Notice: Subject to any disclaimer, the term of this patent is extended or adjusted under 35 U.S.C. 154(b) by 426 days.

This patent is subject to a terminal disclaimer.

(21) Appl. No.: 15/913,608

(22) Filed: Mar. 6, 2018

(65) Prior Publication Data

US 2018/0256279 A1    Sep. 13, 2018

Related U.S. Application Data

(63) Continuation of application No. 15/095,394, filed on Apr. 11, 2016, now Pat. No. 9,937,016, which is a
(Continued)

(51) Int. Cl.
*A61B 90/17* (2016.01)
*A61B 10/02* (2006.01)
(Continued)

(52) U.S. Cl.
CPC ............ *A61B 90/17* (2016.02); *A61B 5/062* (2013.01); *A61B 5/065* (2013.01);
(Continued)

(58) Field of Classification Search
CPC ......... A61B 90/17; A61B 90/50; A61B 5/062; A61B 5/065; A61B 10/0041; A61B 10/0275; A61B 17/3403
(Continued)

(56) References Cited

U.S. PATENT DOCUMENTS

| 4,450,536 A | 5/1984 | Schroeder |
| 4,869,378 A | 9/1989 | Miller |

(Continued)

FOREIGN PATENT DOCUMENTS

| EP | 1410764 A1 | 4/2004 |
| JP | 2004033753 A | 2/2004 |

(Continued)

OTHER PUBLICATIONS

European Search Report dated Jun. 28, 2016, in European Patent Application No. 13856085.9.
(Continued)

*Primary Examiner* — Daniel L Cerioni
(74) *Attorney, Agent, or Firm* — Merchant & Gould P.C.

(57) ABSTRACT

A biopsy device includes a lateral member; a gun mount configured to support a biopsy gun, the gun mount being connected to the lateral member and movable along a first axis with respect to the lateral member, and a sensor which detects a position of the gun mount along the first axis with respect to the lateral member and generates positional data which is provided to an interface module. The gun mount can also be reconfigured in orientations which are offset in a dimension which is orthogonal to the first axis, orientations rotationally offset about the first axis or an axis parallel to the first axis. The lateral member can be in right hand and left hand orientations. Various sensors detect these reconfigurations and provide corresponding data to the interface module for additional calculations and display.

13 Claims, 13 Drawing Sheets

Related U.S. Application Data continuation of application No. 13/611,502, filed on Sep. 12, 2012, now Pat. No. 9,308,017.

(60) Provisional application No. 61/535,401, filed on Sep. 16, 2011.

(51) Int. Cl.

| | | |
|---|---|---|
| *A61B 90/50* | (2016.01) | |
| *A61B 17/34* | (2006.01) | |
| *A61B 5/06* | (2006.01) | |
| *A61B 10/00* | (2006.01) | |
| *A61B 90/00* | (2016.01) | |

(52) U.S. Cl.
CPC ...... *A61B 10/0041* (2013.01); *A61B 10/0275* (2013.01); *A61B 17/3403* (2013.01); *A61B 90/50* (2016.02); *A61B 2010/0208* (2013.01); *A61B 2017/3405* (2013.01); *A61B 2090/376* (2016.02)

(58) Field of Classification Search
USPC .................................................. 600/567
See application file for complete search history.

(56) References Cited

U.S. PATENT DOCUMENTS

| | | | |
|---|---|---|---|
| 4,879,508 | A | 11/1989 | Andermo |
| 5,047,036 | A | 9/1991 | Koutrouvelis |
| 5,053,042 | A | 10/1991 | Bidwell |
| 5,078,140 | A | 1/1992 | Kwoh |
| 5,249,583 | A | 10/1993 | Mallaby |
| 5,280,427 | A | 1/1994 | Magnusson et al. |
| 5,308,352 | A | 5/1994 | Koutrouvelis |
| 5,628,327 | A | 5/1997 | Unger et al. |
| 5,665,095 | A | 9/1997 | Jacobson |
| 5,782,775 | A | 7/1998 | Milliman et al. |
| 6,102,866 | A | 8/2000 | Nields et al. |
| 6,331,437 | B1 | 12/2001 | Cohen |
| 6,447,447 | B1 | 9/2002 | Mitsumori |
| 6,464,648 | B1 | 10/2002 | Nakamura |
| 6,468,226 | B1 | 10/2002 | McIntyre, IV |
| 6,665,554 | B1 | 12/2003 | Charles et al. |
| 6,712,773 | B1 | 3/2004 | Viola |
| 7,438,692 | B2 | 10/2008 | Tsonton et al. |
| 8,123,697 | B2 | 2/2012 | Daum et al. |
| 8,932,233 | B2 | 1/2015 | Haberstich et al. |
| 8,945,014 | B2 | 2/2015 | Zan |
| 9,308,017 | B2 | 4/2016 | Girgenti et al. |
| 9,314,926 | B2 | 4/2016 | Bailey et al. |
| 9,937,016 | B2 | 4/2018 | Girgenti et al. |
| 2002/0065462 | A1 | 5/2002 | Brabrand et al. |
| 2002/0151820 | A1 | 10/2002 | Dvorak et al. |
| 2003/0073895 | A1 | 4/2003 | Nields et al. |
| 2003/0199785 | A1 | 10/2003 | Hibner et al. |
| 2004/0077972 | A1 | 4/2004 | Tsonton et al. |
| 2005/0085838 | A1 | 4/2005 | Thompson et al. |
| 2005/0261581 | A1 | 11/2005 | Hughes et al. |
| 2006/0241385 | A1 | 10/2006 | Dietz |
| 2006/0261571 | A1 | 11/2006 | Mitchell |
| 2007/0016067 | A1 | 1/2007 | Webster, III et al. |
| 2007/0032723 | A1 | 2/2007 | Glossop |
| 2008/0045833 | A1 | 2/2008 | Defreitas et al. |
| 2009/0030339 | A1 | 1/2009 | Cheng et al. |
| 2009/0131824 | A1 | 5/2009 | Andrisek et al. |
| 2009/0171244 | A1 | 7/2009 | Ning et al. |
| 2009/0323892 | A1 | 12/2009 | Hitzke et al. |
| 2010/0036245 | A1 | 2/2010 | Yu et al. |
| 2010/0160810 | A1 | 6/2010 | Parihar et al. |
| 2011/0015517 | A1 | 1/2011 | Hughes |
| 2011/0087132 | A1 | 4/2011 | DeFreitas et al. |
| 2011/0112540 | A1 | 5/2011 | McLean et al. |
| 2011/0118625 | A1 | 5/2011 | Akuzawa et al. |
| 2012/0007863 | A1 | 1/2012 | Endo et al. |
| 2012/0010512 | A1 | 1/2012 | O'Laughlin et al. |
| 2012/0298820 | A1* | 11/2012 | Manolidis ............ A61B 90/50 248/222.14 |
| 2013/0072816 | A1 | 3/2013 | Girgenti et al. |
| 2013/0158565 | A1 | 6/2013 | Anvari et al. |
| 2015/0313674 | A1 | 11/2015 | DeFreitas et al. |
| 2016/0296298 | A1 | 10/2016 | Girgenti |
| 2017/0079720 | A1 | 3/2017 | Velusamy et al. |

FOREIGN PATENT DOCUMENTS

| | | |
|---|---|---|
| WO | 0028882 A2 | 5/2000 |
| WO | 0241794 A1 | 5/2002 |
| WO | 2010113633 A1 | 10/2010 |
| WO | 2013040017 A1 | 3/2013 |
| WO | 2014081908 A1 | 5/2014 |

OTHER PUBLICATIONS

International Search Report dated Nov. 29, 2012, from corresponding PCT Application No. PCT/US12/54835.

International Preliminary Report on Patentability dated Mar. 18, 2014, from corresponding PCT Application No. PCT/US12/54835.

Supplementary European Search Report dated Feb. 5, 2015, in corresponding European Patent Application No. EP 12 83 2632.

European Communication in Application 12832632.9, dated Jan. 2, 2018, 5 pages.

European Communication in Application 12832632.9, dated Feb. 26, 2019, 5 pages.

\* cited by examiner

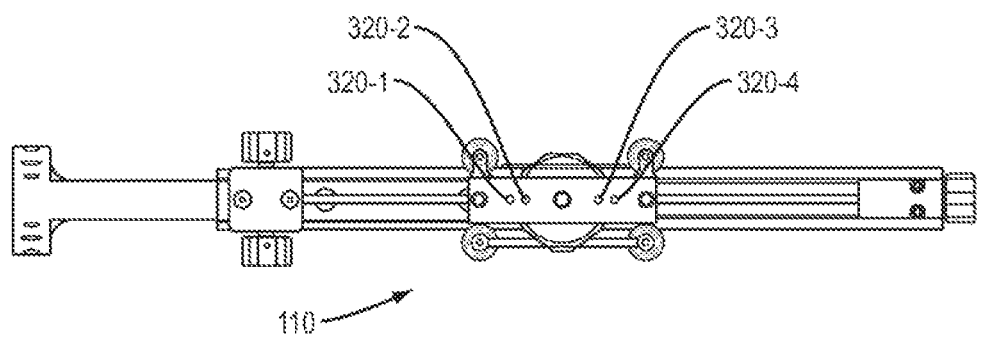
FIG. 22
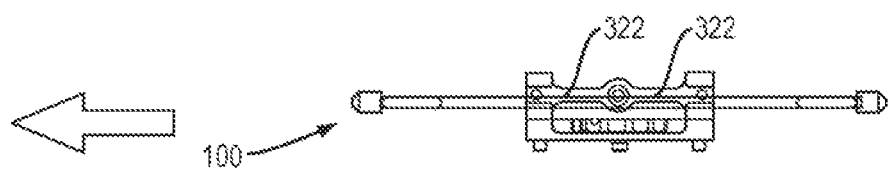
FIG. 23
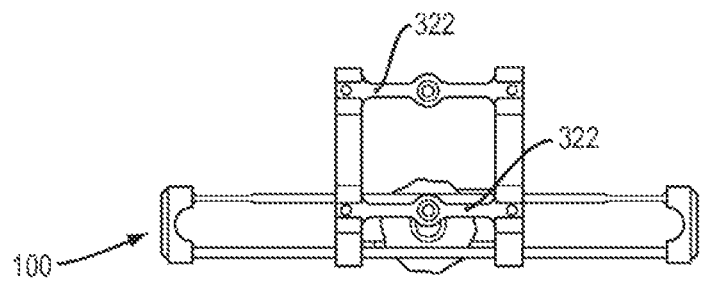
FIG. 24
| COMBINATION | SENSORS | | | |
|---|---|---|---|---|
| | 1 | 2 | 3 | 4 |
| VERTICAL, RIGHT, STANDARD | X | | | |
| VERTICAL, RIGHT, OFFSET | | | X | |
| VERTICAL, LEFT, STANDARD | | X | | |
| VERTICAL, LEFT, OFFSET | | | | X |
| HORIZONTAL, RIGHT, STANDARD | X | | X | |
| HORIZONTAL, LEFT, STANDARD | | X | | X |
FIG. 25

BREAST BIOPSY LATERAL ARM SYSTEM

CROSS-REFERENCE TO RELATED APPLICATIONS

The present application is a continuation of U.S. patent application Ser. No. 15/095,394, inventors John Girgenti et al., filed Apr. 11, 2016, now U.S. Pat. No. 9,937,016, which, in turn, is a continuation of U.S. patent application Ser. No. 13/611,502, inventors John Girgenti et al., filed Sep. 12, 2012, now U.S. Pat. No. 9,308,017, which, in turn, claims priority under 35 U.S.C. 119(e) to U.S. Provisional Patent Application No. 61/535,401 titled Breast Biopsy Lateral Arm System, inventors John Girgenti et al., filed Sep. 16, 2011, the disclosures of all of which are incorporated herein by reference in their entireties.

BACKGROUND

The subject matter of this disclosure is generally related to the medical field. Medical imaging technologies such as stereotactic x-ray, fluoroscopy, computer tomography, ultrasound, nuclear medicine and magnetic resonance imaging enable detection of small abnormalities in the body of a patient. The discovery of certain abnormalities may prompt performance of a biopsy procedure to a tissue sample for lab analysis to help diagnose and treat patients suspected of having cancerous tumors, pre-malignant conditions or other diseases or disorders. A stereotactic guided percutaneous breast biopsy is often preferable to an open surgical breast biopsy in the case of small abnormalities located deep within the body because a percutaneous biopsy removes a relatively small amount of tissue. For example, a needle can be used to remove individual cells or clusters of cells in the case of fine needle aspiration (FNA), and a core or fragment of tissue in the case of a core biopsy. One difficulty associated with such procedures is that it is necessary to locate the biopsy needle with considerable precision in order to obtain a suitable sample of a small abnormality, particularly if it is located deep within the body. Biopsy guns and guidance systems have been developed to facilitate accurate location of a biopsy needle. However, while these devices offer some advantages, manual computations may be required for configuration. Further, systems may only be suitable for use with certain patients due to size and reconfiguration limitations.

SUMMARY

In accordance with an aspect an apparatus comprises: a lateral member; a gun mount configured to support a biopsy gun, the gun mount being connected to the lateral member and movable along a first axis with respect to the lateral member; and a sensor which detects a position of the gun mount along the first axis with respect to the lateral member and generates positional data which is provided to an interface module.

In accordance with another aspect a method comprises: mounting a biopsy gun in a gun mount connected to a lateral member; moving the biopsy gun along a first axis with respect to the lateral member; and detecting a position of the gun mount along the first axis with respect to the lateral member with a sensor; and generating positional data which is provided to an interface module and presented to an operator.

In addition to allowing reconfiguration of the position of the gun mount along the first axis with respect to the lateral member, and detection of the position of the gun, the gun mount can advantageously be connected to the lateral member in standard and offset orientations which are offset in a dimension which is orthogonal to the first axis. Further, the gun mount is configured to interchangeably support the biopsy gun in either a vertical orientation or a horizontal orientation, the vertical orientation being rotationally offset from the horizontal orientation by 90 degrees about the first axis or an axis parallel to the first axis. Moreover, the lateral member can be interchangeably attached to a first stabilizing feature in right hand and left hand orientations which are rotationally offset by 180 degrees. Various sensors detect these reconfigurations and provide corresponding data that can be displayed to an operator via the interface module. Further, the interface module can use the data to calculate and display information such as needle aperture position based on known characteristics of the mounted biopsy gun. Still further, the interface module can compare configuration data with a planned configuration to automatically verify that the configuration is appropriate.

Other features and advantages will become apparent to those of ordinary skill in the art in view of the figures and detailed description.

BRIEF DESCRIPTION OF THE FIGURES

FIG. 22 illustrates a gun mount and orientation sensing feature.

FIG. 23 illustrates a horizontal gun mount configuration with respect to FIG. 22.

FIG. 24 illustrates a vertical gun mount configuration with respect to FIG. 22.

FIG. 25 illustrates a table of potential configurations and corresponding sensor indications.

DETAILED DESCRIPTION

Figure 1:
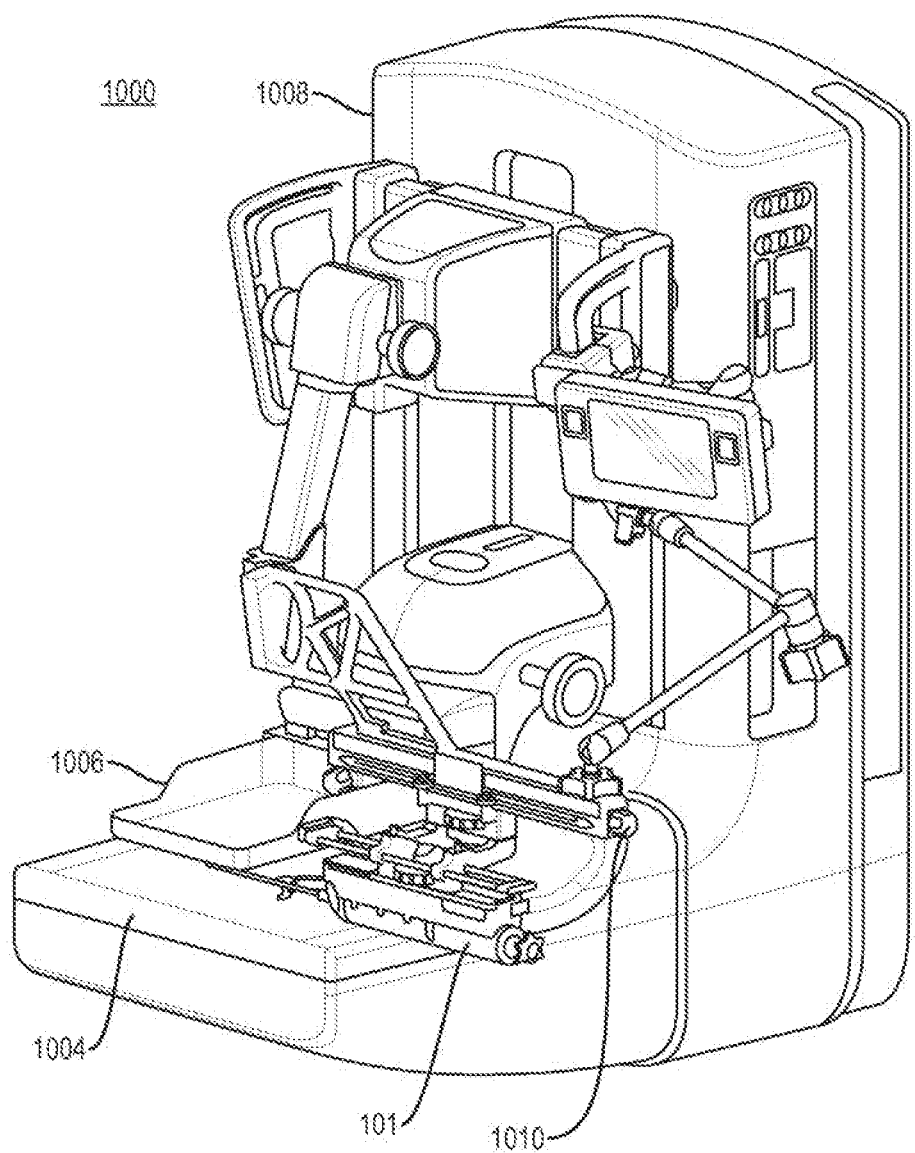
FIGS. 1 and 2 illustrate a breast biopsy station.
Figure 2:
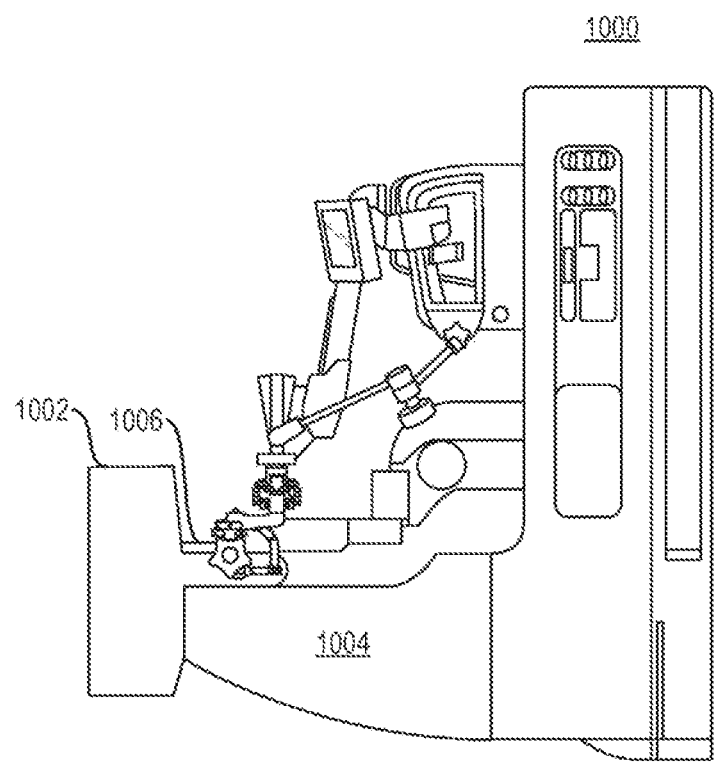
Figure 3:
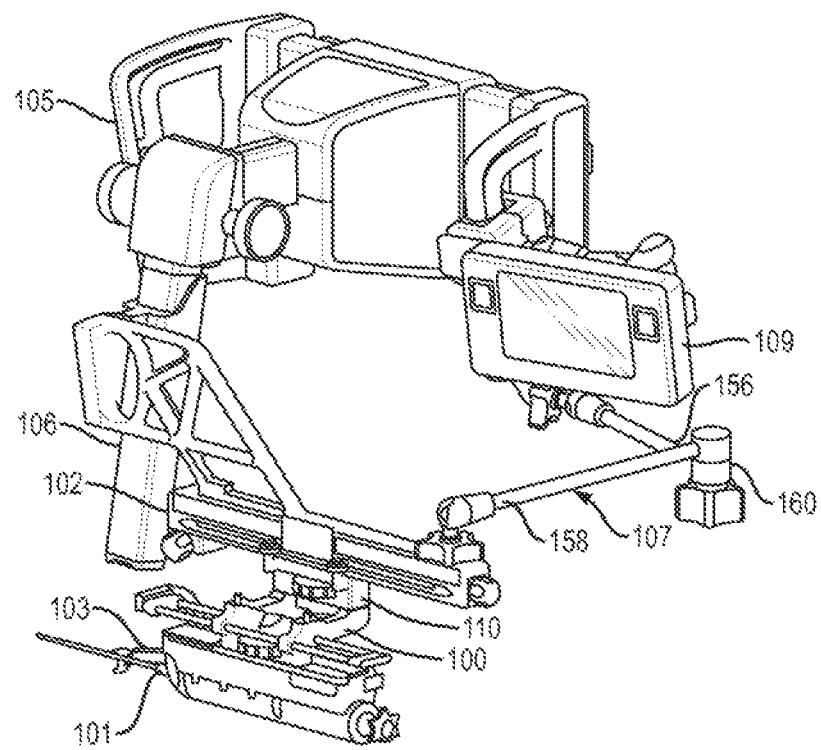
FIG. 3 is an isometric view of a lateral arm needle guide for stereotactic biopsy.
Figure 4:
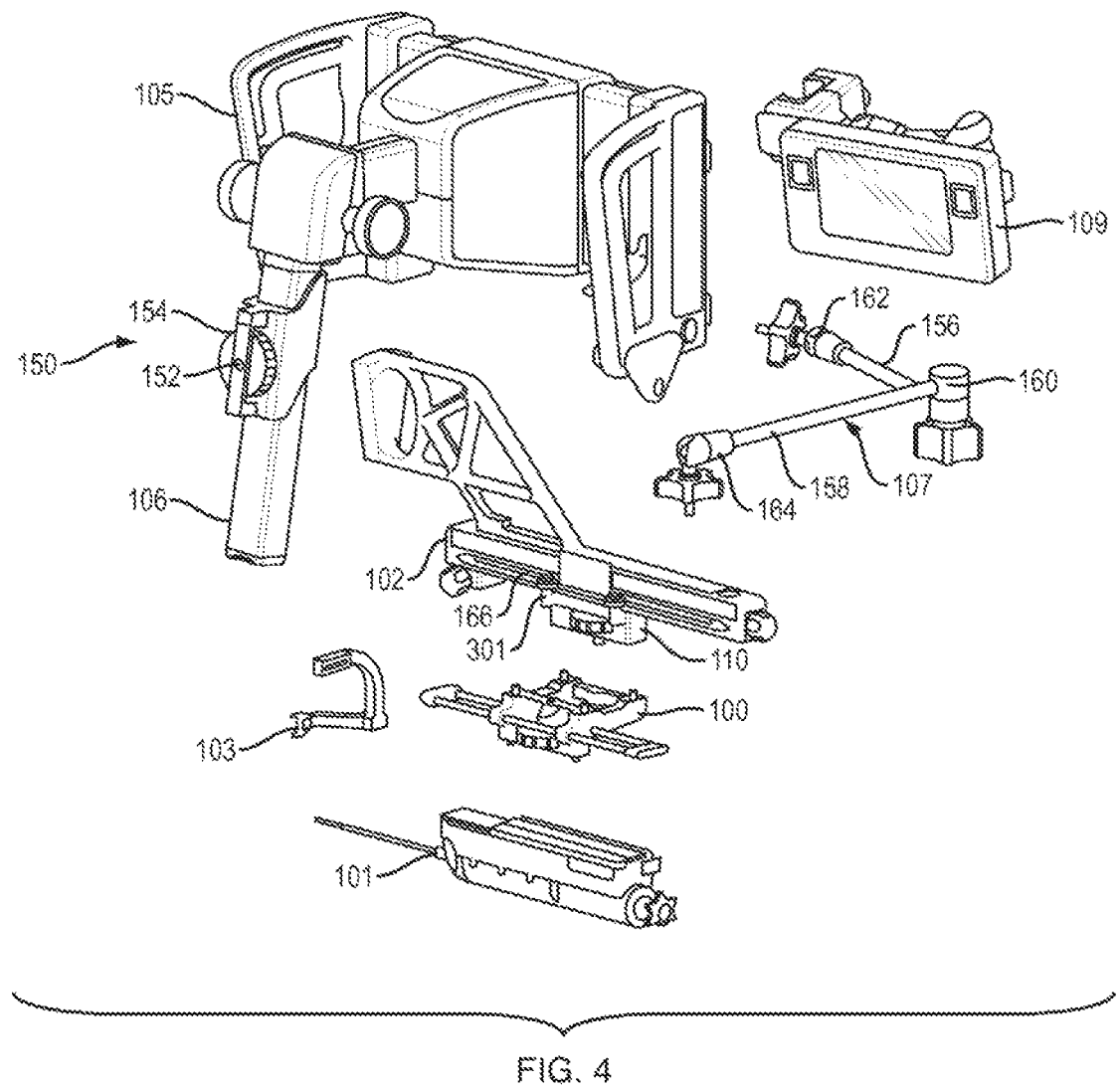
FIG. 4 is an exploded view of the lateral arm needle guide of FIG. 3.
Figure 5:
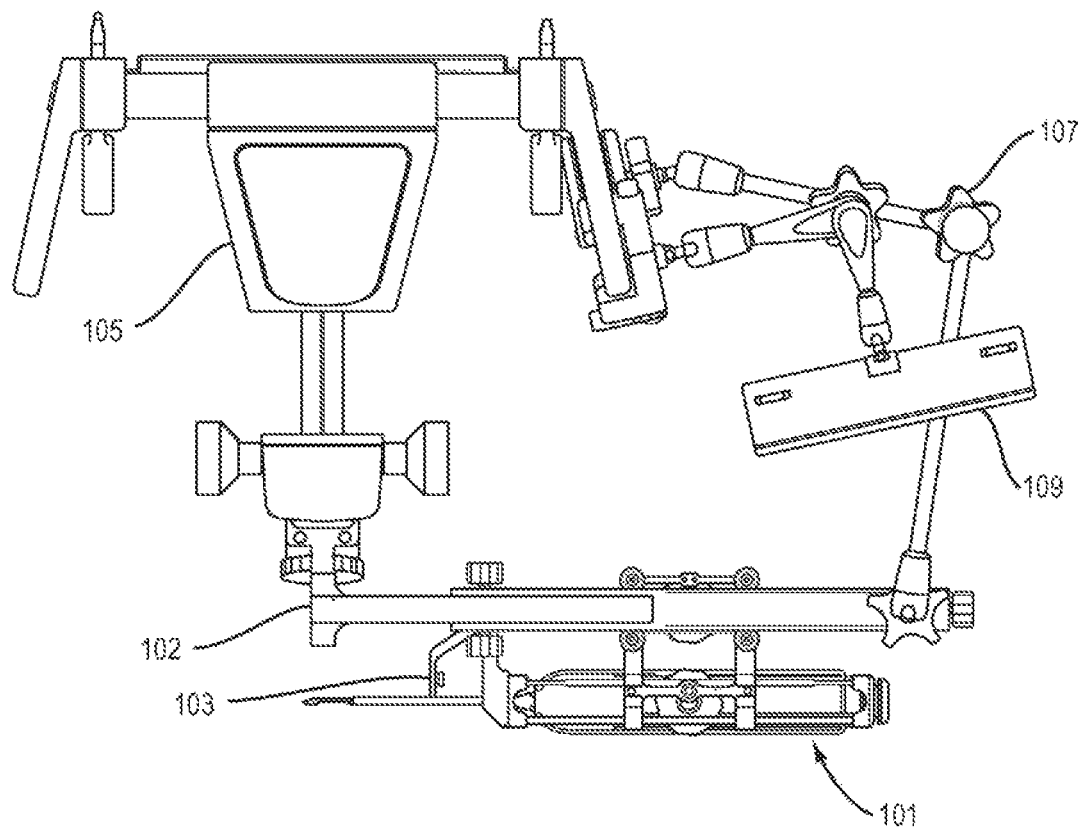
FIG. 5 is a top view of the lateral arm needle guide of FIG. 3.
Figure 6:
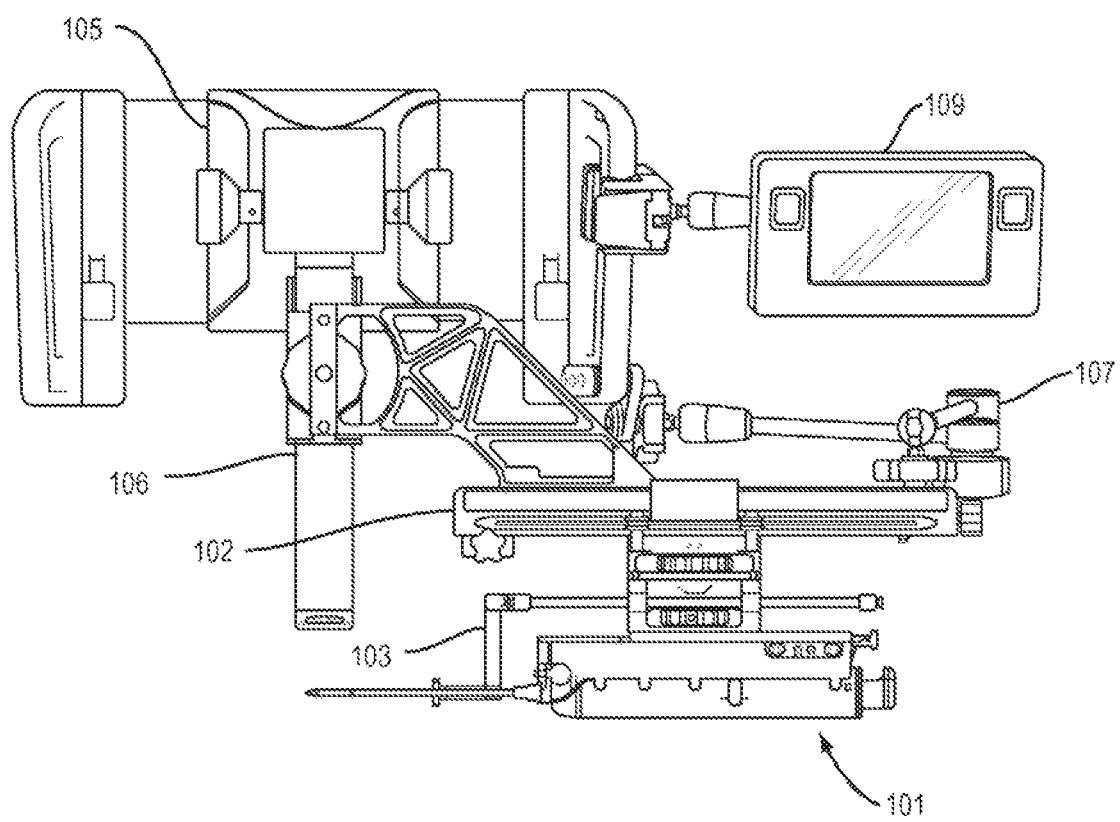
FIG. 6 is a front view of the lateral arm needle guide of FIG. 3.

FIGS. 1 and 2 illustrate a breast biopsy station 1000. The patient is positioned with her chest wall 1002 against the breast platform 1004 and compression paddle 1006. The patient's breast is positioned on the breast platform and placed under compression by a compression paddle, i.e., the breast is between the platform and the compression paddle. A radiographic imaging system 1008 produces an image of the breast in order to locate a feature of interest, e.g., a lesion. An integrated guided biopsy needle control device 1010 is used to obtain a tissue sample of the feature of interest. More particularly, the biopsy needle control device displays information about the location of the targeted feature and the biopsy gun 101 to help position the biopsy gun to where the operational path of the needle intersects with the target feature.

FIGS. 3, 4, 5 and 6 illustrate the needle control device 1010 (FIG. 1) in greater detail. The device includes a gun mount 100, lateral arm 102, needle guide 103, biopsy guidance module 105, support arm 107, control module 109, and slide assembly 110. The gun mount 100 is connected to the slide assembly 110. The slide assembly 110 is connected to the lateral arm 102. The lateral arm 102 is connected to the biopsy guidance module 105 via both a post member 106 of the biopsy guidance module and an optional articulating support arm 107. The biopsy control module 109 is also connected to the biopsy guidance module 105.

The gun mount 100 is configured to position and secure a selected biopsy gun 101. More particularly, an operator can securely mount and remove any of various biopsy guns that might be selected, so different biopsy guns may be utilized as needed. Indexing features help assure that the biopsy gun can be predictably and repeatedly mounted in a particular position with respect to the gun mount when mounted. The biopsy gun 101 is operative in response information from an embedded computer, information provided by an operator via the biopsy guidance module 105 and biopsy control module 109, and sensor input that will be described below to locate a biopsy needle of the biopsy gun to obtain a tissue sample, e.g., by inserting an outer cannula into a predetermined location of interest within the patient, extracting a tissue core sample by moving an inner cannula relative to the outer cannula, and removing the needle from the patient. The needle guide 103 helps to guide the outer cannula of the biopsy gun, e.g., by inhibiting deflection. Various types of biopsy guns and needles are known, and the functioning of biopsy guns and needles in obtaining tissue cores is well understood in the art. Therefore, these features will not be described in greater detail. As will be described in greater detail below, aspects of the lateral arm needle guide device include interface features which calculate, utilize and display useful information, reconfiguration features which allow secure repositioning of the selected biopsy gun, and sensing features which detect certain reconfiguration and repositioning data in order to facilitate the biopsy procedure, e.g., by providing the data to the biopsy guidance module and biopsy control module in order to automate calculation of offsets, adjustments and other information that helps to obtain tissue cores from a specific location. Moreover, the data can be used to verify that a configuration entered by an operator matches the actual configuration of the device.

Identifying characteristics of the particular gun and needle being used can be entered by the operator via the biopsy control module 109, e.g., model number, individual device identifier, performance characteristics, etc. The biopsy guidance and control modules include at least one embedded computer with a processor and potentially other processing hardware, and software stored on non-transitory computer readable memory. A database of characteristics of various biopsy guns and needles may also be stored in the memory. The known characteristics of the biopsy gun (including the needle) can be used by the embedded computer to help calculate and display information to assist the operator as will be explained below.

One aspect of repositioning the biopsy gun 101 is via movement of the lateral arm 102. The lateral arm is repositionable with respect to the biopsy guidance module 105. In particular, the biopsy guidance module 105 includes a clamp member 150 which can be slidably moved along and secured to the post member 106 at any of various locations along the length of the post member. Moreover, the clamp member 150 includes a threaded fastening member 152 attached to a knob 154 for securing a distal end of the lateral arm 102 to the clamp member, thereby fixing the location of the lateral arm 102 relative to the biopsy guidance module 105. The position of the biopsy gun and lateral arm with respect to the biopsy guidance module is made even more stable and secure with assistance from the articulating arm support 107, if the support arm is present. In the illustrated example the optional articulating arm support includes two support arms 156, 158 connected at distal ends via a lockable attachment 160 which can pivot in two-dimensions. Moreover, the other distal end of the first arm 156 is attached to the biopsy guidance module via a lockable attachment 162 which can pivot in three-dimensions, and the other distal end of the second arm 158 is attached to the lateral arm 102 via a lockable attachment 164 which can pivot in three-dimensions. Consequently, the lateral arm is free to move with the clamp member 150 relative to the post member 106 when the pivoting attachments 160, 162, 164 are in an unlocked, free-moving state. When the clamp member 150 is secured to the post member 106 and the lateral arm 102, additional support is provided by turning the knobs of the pivoting attachments to change their state from the unlocked free-moving state to a locked non-moving state. This results in the biopsy gun 101 being repositionable via movement of the lateral arm, with stable multi-point support of the lateral arm at different distal ends when the lateral arm is secured in position relative to the biopsy guidance module.

Another aspect of repositioning the biopsy gun 101 is moving the gun relative to the lateral arm 102. Parallel rails 166 are disposed on opposite sides of the lateral arm (only the near side rail shown). The slide assembly 110 includes four rotatable wheels 301 which engage and ride along the rails (two wheels on each rail) and allow the slide assembly to slidably move along the rails with respect to the lateral arm. Locking features which will be described below in greater detail allow the slide assembly to be secured in a desired position relative to the rails when in a locked state. More particularly, when the locking features are in an unlocked state the slide assembly is free to move slidably along the rails but is otherwise secured to the lateral arm by the wheels and rails. The gun mount 100 can be secured to the slide assembly via threaded fastening members, and the biopsy gun can be secured to the gun mount. Consequently, when the locking features are unlocked the biopsy gun can be moved slidably along an X-Axis with respect to the lateral arm, and the biopsy gun can be secured in position relative to the lateral arm when the locking features are locked.

Figure 7:
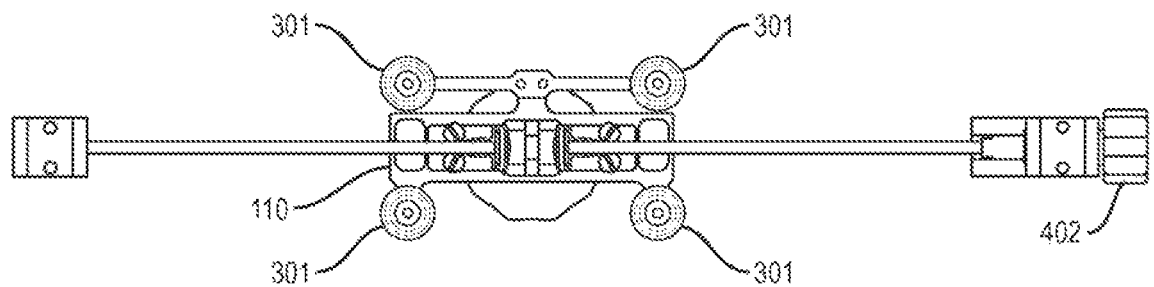
FIG. 7 illustrates an X-Axis slide lock for the slide assembly of the lateral arm needle guide.
Figure 8:
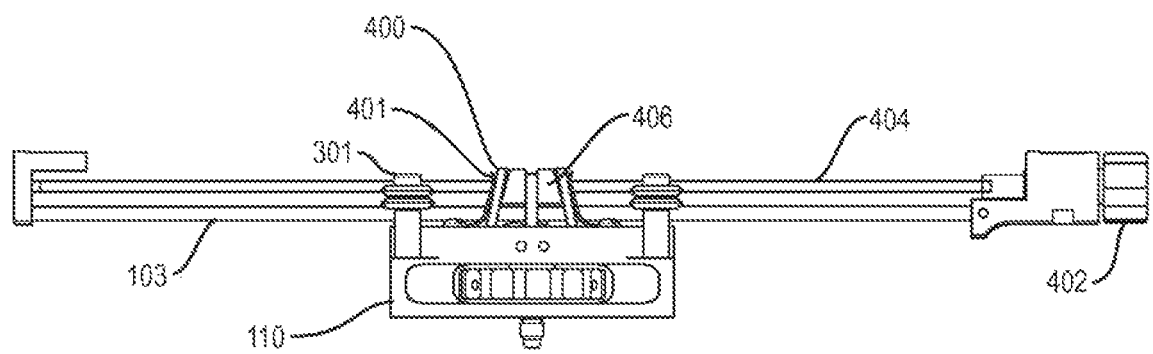
FIG. 8 is a front view of the X-Axis slide lock of FIG. 7 in the locked state.
Figure 9:
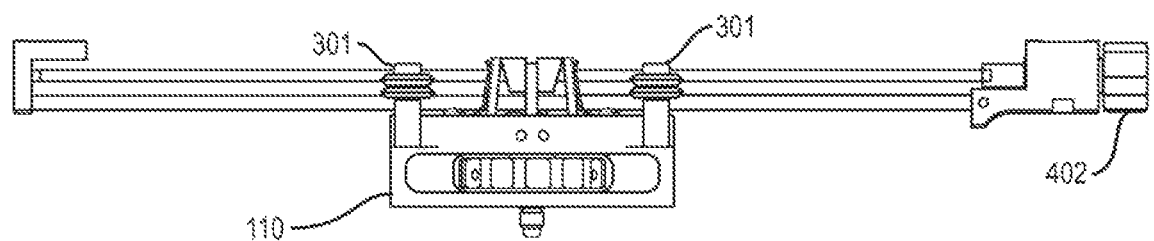
FIG. 9 is a front view of the X-Axis slide lock of FIG. 7 in the unlocked state.

FIGS. 7, 8 and 9 illustrate a slide assembly 110 locking feature including an X-Axis slide lock. As mentioned above, the slide assembly 110 includes four grooved wheels 301 that ride along rails 166 (FIG. 1B) disposed on opposite sides of the lateral arm 102 along the X-axis. The illustrated X-axis slide lock mechanism utilizes a spring loaded locking plate 400 (note spring 401) to leverage against a round locking shaft 103 to hold the X-Axis position of the slide assembly 110 in any of an infinite number of positions along its length of travel along the rails. The lock/release interface is a knob 402 at the end of a square cam drive shaft 404. The lock/release is actuated by turning the knob 402 through 180 degrees, which fixes the slide assembly in a location that does not traverse the X-Axis because of friction between the round shaft 103 and the locking plates 400 which are actuated by the lock/release cam 406. This advantageously allows the slide assembly to be securely and easily locked in place, which is helpful because needle position can be affected during insertion if the position of the biopsy gun is insecure.

Figure 10:
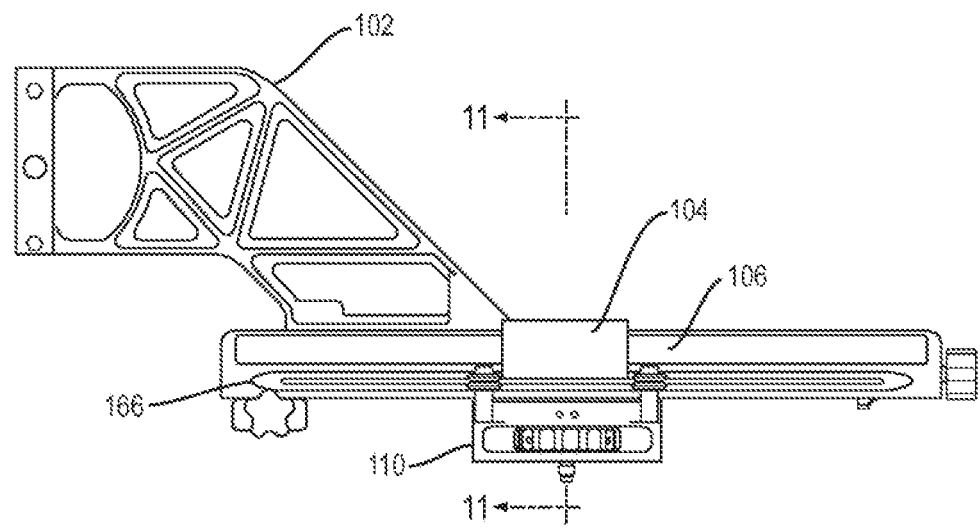
FIG. 10 illustrates an X-Axis position indication feature for the lateral arm and gun mount.
Figure 11:
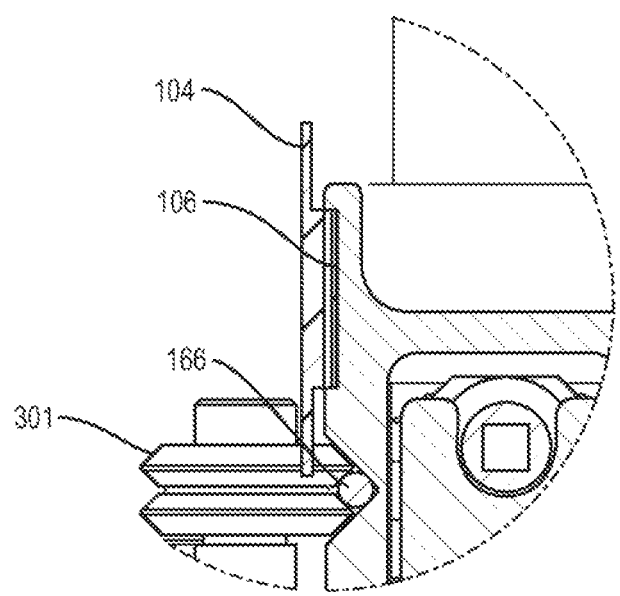
FIG. 11 is a cross-sectional view of the lateral arm and gun mount of FIG. 8 taken along A-A.
Figure 12:
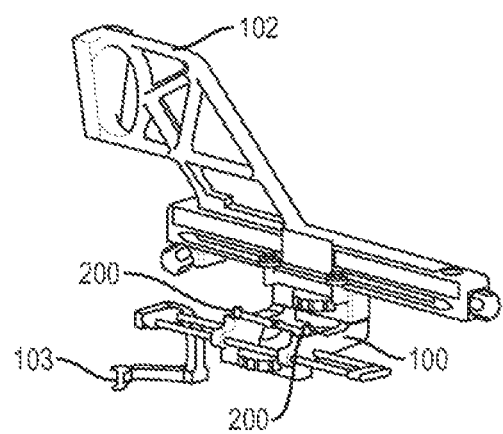
FIG. 12 is an isometric view of the lateral arm, gun mount and needle guide in a standard position.
Figure 13:
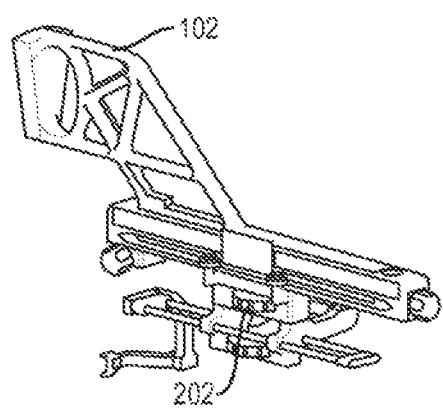
FIG. 13 is an isometric view of the lateral arm, gun mount and needle guide in an offset position.
Figure 14:
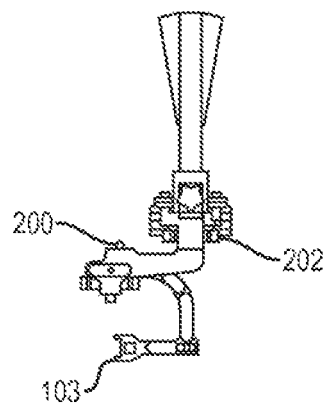
FIG. 14 is a front view of the lateral arm, gun mount and needle guide in the standard position.
Figure 15:
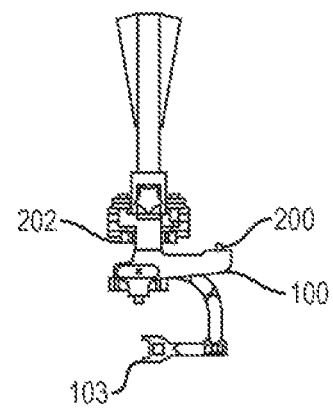
FIG. 15 is a front view of the lateral arm, gun mount and needle guide in the offset position.
Figure 16:
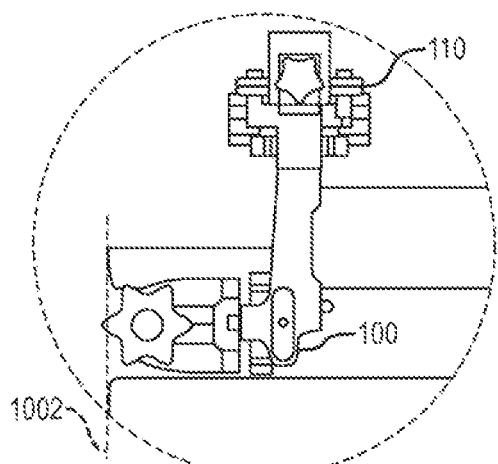
FIGS. 16, 17 and 18 further illustrate the standard and offset gun mount positions.
Figure 17:
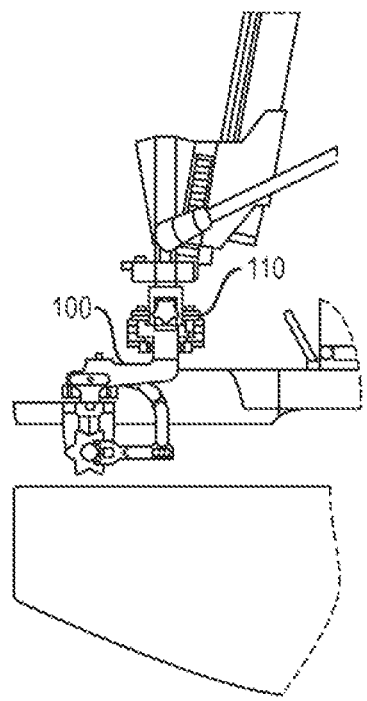
Figure 18:
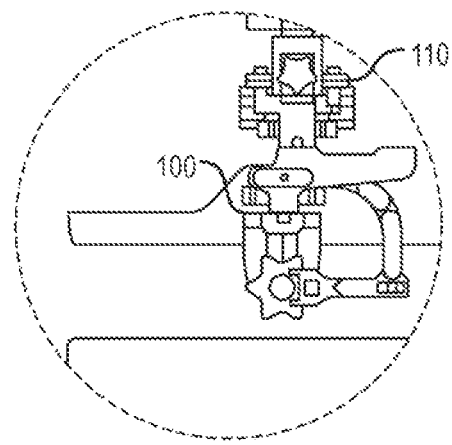

FIGS. 10 and 11 illustrate a sensor feature for detecting the X-Axis position of the slide assembly 110 relative to the lateral arm 102. The sensor feature generates data indicative of the position of the slide assembly relative to the lateral arm, and transmits that data to the biopsy guidance module and biopsy control module. As previously mentioned, the slide assembly 110 includes grooved wheels 301 that ride along rails 166 attached to opposite sides of the lateral arm 102. The slide assembly includes an active position sensing circuit board 104 which is proximate to a side of the lateral arm. A corresponding passive reference circuit board 106 is disposed on that side of the lateral arm. In particular, the active position sensing circuit is positioned adjacent to the passive reference circuit board such that the active position sensing circuit board 104 can detect position with respect to the corresponding passive reference circuit board 106. Suitable absolute position encoders are known; see, for example, U.S. Pat. No. 4,879,508, issued Nov. 7, 1989. As the active position sensing circuit board travels with the slide assembly it generates absolute X-axis position data of the gun mount (and thus the biopsy gun) relative to the lateral arm rail. The position data is provided to the embedded computer of the biopsy guidance module to enable calculation and display of information based on the X-axis position data, the known characteristics of the mounted biopsy gun and needle combination, or both. For example, needle aperture position may be calculated and displayed on the biopsy control module. This will advantageously help to obviate the need for the doctor or technician to manually calculate the needle aperture position, e.g., from the position as read from a visible scale mounted on the lateral arm.

FIGS. 12, 13, 14, 15, 16, 17, and 18 illustrate a Y-axis reconfiguration feature. The gun mount 100 includes a secondary fastening member so that the gun mount can be detached from the lateral arm slide assembly 110 in a standard position (shown in FIGS. 12, 14) and re-attached at an offset position (shown in FIGS. 13, 15). The needle guide 103 can be detached and re-attached to the gun mount as needed per procedure configuration. The two mounting positions (standard, offset) are offset along the Y-axis. This advantageously allows the biopsy gun needle to be positioned farther back from the chest wall 1002 of the patient when desirable. More particularly, this helps accommodate a wider range of breast sizes, e.g., utilizing the offset position for larger breasts. In the illustrated example each mounting position includes two location pins 200 on the gun mount which are inserted into corresponding sockets in the lateral arm. The slide assembly includes a captive machine screw and integral knob 202. The machine screw is secured to threaded socket(s) in the gun mount. Note that FIGS. 16 and 18 also illustrate a vertical/horizontal gun mount reconfiguration that will be described in greater detail below.

Figure 19:
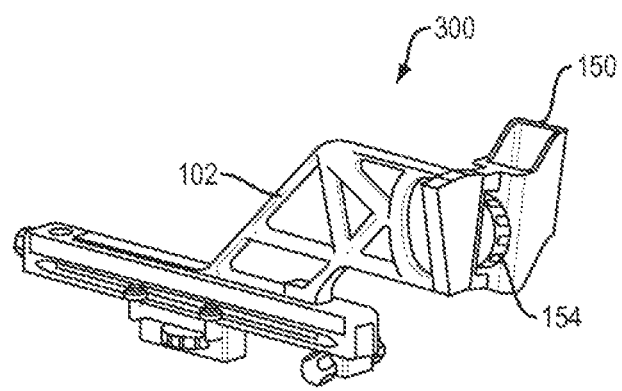
FIG. 19 illustrates the lateral arm configured for a left hand (LH) procedure.
Figure 20:
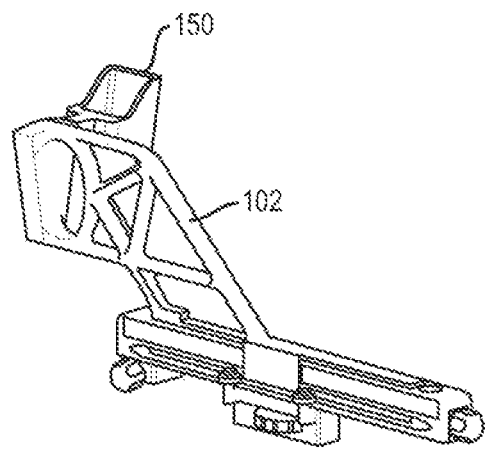
FIG. 20 illustrates the lateral arm configured for a right hand (RH) procedure.
Figure 21:
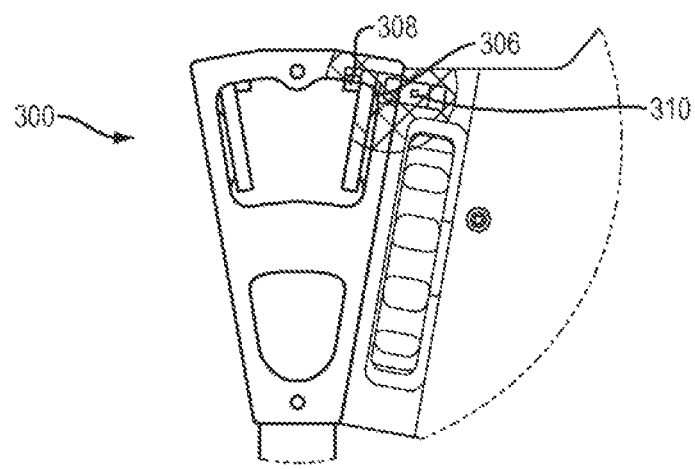
FIG. 21 illustrates a LH/RH configuration sensing feature.

FIGS. 19, 20 and 21 illustrate a sensor feature 300 that detects lateral arm mounting configuration. As previously described, the biopsy guidance module 105 (FIG. 3) includes a clamp member 150 which can be slidably moved along and secured to the post member at any of various locations along the length of the post member. The clamp member 150 includes guide posts and a threaded fastening member actuated by a knob 154 for positioning and securing the clamp member relative to the lateral arm 102. The lateral arm includes corresponding smooth and threaded sockets for receiving the guide posts and threaded fastening member. Moreover, different sets of such locating and securing features are provided on opposite sides of the lateral arm, thereby allowing the lateral arm to be secured to the clamp member (and thus the biopsy guidance module) in either a left hand (LH) or right hand (RH) orientation. The sensing feature 300 automatically detects whether the lateral arm 102 is configured for a left hand (LH) procedure (as shown in FIG. 19) or a right hand (RH) procedure (as shown in FIG. 20). The sensing feature provides this data to the embedded computer of the biopsy control and biopsy guidance modules. The embedded computer can display the data for the user and use the data to verify that the lateral arm components have been installed according to the selected procedure entered by the operator via the biopsy control module. The illustrated sensing feature utilizes analog Hall Effect sensors 306 with a fixed magnet 308. When a dowel pin 310 of magnetizable material (as integrated into a Biopsy Guidance Module Z-Axis Gun Mount) is within a close proximity of the sensor/magnet pair, the magnetic flux level passing through the sensor increases. The levels at which the pin is and is not detected as being present are recorded by the embedded computer and are used to determine the RH/LH mounting orientation based on which sensor is closest to a dowel pin. This advantageously enables automatic verification of configuration for LH and RH procedures.

FIGS. 16, 18, 22, 23 and 24 illustrate vertical/horizontal gun mount reconfiguration and a gun mount type and orientation sensing feature. As previously described, the gun mount 100 is connected to the slide assembly 110. Proper orientation and secure attachment can be accomplished with a threaded fastening member, threaded socket, and one or more guide posts and corresponding smoothbore sockets. Moreover, separate sets of such positioning and securing feature are provided on both a side and a bottom of the slide assembly to permit both horizontal and vertical mounting. FIG. 23 specifically shows the horizontal gun mount position with respect to FIG. 22. FIG. 24 specifically shows the vertical gun mount position with respect to FIG. 22. The threaded fastening member may be actuated by a knob in order to facilitate reconfiguration between the horizontal and vertical positions. The illustrated sensing feature utilizes bipolar or unipolar digital Hall Effect sensors 320-1, 320-2, 320-3, 320-4 to detect magnets 322 when in close proximity. Four sensors are used in specific locations to determine which type of gun mount is attached and in which orientation, e.g., horizontal gun mount orientation or vertical gun mount orientation. Two magnets are permanently installed in each gun mount.

Referring to FIG. 25, the locations of sensors and magnets, e.g., as depicted in FIGS. 22, 23 and 24, enable detection of each of six different potential configuration combinations. The sensor data is provided to the embedded computer of the biopsy control and guidance modules to enable display of the detected configuration and automatic configuration verification for horizontal or vertical gun mounts in either left hand or right hand configurations for both standard and offset positions. For verification purposes the operator may be required to enter a planned configuration via the biopsy control module before performing the biopsy procedure. The entered planned configuration would be compared with the sensor data by the guidance or control module in order to verify that the actual device configuration matches the planned configuration. If the actual and planned configurations do not match then an alert may be provided to the operator. For example, the non-matching configuration parameters might be displayed on the biopsy control module.

While the invention has been described through the above examples and features, it will be understood by those of ordinary skill in the art that a wide variety of modifications, combinations and variations of the examples and features may be made without departing from the inventive concepts herein disclosed. Moreover, the invention should not be viewed as being limited to any specific purposes described herein, but rather should be viewed as being applicable to accomplish a wide variety of purposes beyond those described herein.

The invention claimed is:

1. A breast biopsy system comprising:
a lateral member, the lateral member being mounted on a post member of a biopsy guidance module, wherein the lateral member has a first axis;
a slide assembly having a length along a longitudinal axis, wherein the slide assembly is slidably mounted on the lateral member, wherein the longitudinal axis of the slide assembly is generally parallel to the first axis of the lateral member; and
a gun mount configured to support a biopsy gun, the gun mount being mountable on the slide assembly and being connected to the lateral member via the slide assembly, wherein the gun mount is movable by sliding the slide assembly along the first axis with respect to the lateral member, the first axis being along an insertion direction of the biopsy gun into a patient, wherein the gun mount comprises a first mounting element, wherein the slide assembly comprises alternative sets of a second mounting element, the second mounting element being complementary to the first mounting element, one of the alternative sets of the second mounting element being located on a side of the slide assembly, another of the alternative sets of the second mounting element being located on a bottom of the slide assembly, whereby the gun mount is configured to interchangeably support the biopsy gun in either a vertical orientation or a horizontal orientation, depending on to which of the alternative sets of the second mounting element the first mounting element is mounted, the vertical orientation being rotationally offset from the horizontal orientation by 90 degrees about the first axis or an axis parallel to the first axis.

2. The breast biopsy system of claim 1 further comprising a biopsy guidance module.

3. The breast biopsy system of claim 1 further comprising a stabilizing feature which fastens the lateral member at an attachment point to the post member.

4. The breast biopsy system of claim 3 wherein the lateral member is interchangeably attached to the stabilizing feature in right hand and left hand orientations which are rotationally offset by 180 degrees.

5. The breast biopsy system of claim 4 wherein the stabilizing feature includes a threaded fastening member.

6. The breast biopsy system of claim 1 wherein the gun mount is configured to support the biopsy gun in vertical and horizontal orientations.

7. The breast biopsy system of claim 1 further comprising an interface module.

8. The breast biopsy system of claim 7 wherein the interface module uses positional data to calculate and display a needle aperture position based on known characteristics of the mounted biopsy gun.

9. The breast biopsy system of claim 7 wherein the interface module includes a computer which determines at least one characteristic of the biopsy gun based on operator input in the interface module.

10. The breast biopsy system of claim 1 further comprising a first sensor, a second sensor, and a third sensor, the first sensor detecting a position of the gun mount along the first axis with respect to the lateral member and generating positional data which is provided to an interface module, the second sensor detecting one of (i) whether the gun mount is configured to support the biopsy gun in the vertical or horizontal orientation, (ii) whether the lateral member is in the left hand or right hand orientation, and (iii) whether the gun mount is connected to the lateral member in the first or second orientation, and generating corresponding data that is provided to the interface module, and the third sensor detecting another one, different from the first sensor, of (i) whether the gun mount is configured to support the biopsy gun in the vertical or horizontal orientation, (ii) whether the lateral member is in the left hand or right hand orientation, and (iii) whether the gun mount is connected to the lateral member in the first or second orientation, and generating corresponding data that is provided to the interface module.

11. The breast biopsy system of claim 7 further comprising a sensor, the sensor being positioned to detect a position of the gun mount along the first axis with respect to the lateral member and generating positional data which is provided to the interface module.

12. The breast biopsy system of claim 7 further comprising a sensor, the sensor being positioned to detect whether the gun mount is configured to support the biopsy gun in the vertical or horizontal orientation and generating corresponding data that is provided to the interface module.

13. The breast biopsy system of claim 7 further comprising a sensor, the sensor being positioned to detect whether the lateral member is in the left hand or right hand orientation and generating corresponding data that is provided to the interface module.

* * * * *